United States Patent
Paul et al.

(10) Patent No.: US 6,375,994 B1
(45) Date of Patent: Apr. 23, 2002

(54) PREPARATION OF FIBER, L-GLUTAMINE AND A SOY DERIVATIVE FOR THE PURPOSE OF ENHANCEMENT OF ISOFLAVONE BIOAVAILABILITY

(75) Inventors: Stephen M. Paul, Rancho Santa Margarita; Charles C. Hsu, Long Beach; Qing-Fu Hu; Daniel Shu, both of Laguna Niguel; Melissa See, Long Beach, all of CA (US)

(73) Assignee: Sun Ten Laboratories, Inc., Irvine, CA (US)

( * ) Notice: Subject to any disclaimer, the term of this patent is extended or adjusted under 35 U.S.C. 154(b) by 0 days.

(21) Appl. No.: 09/641,751

(22) Filed: Aug. 18, 2000

Related U.S. Application Data
(60) Provisional application No. 60/150,018, filed on Aug. 20, 1999.

(51) Int. Cl.$^7$ ............................ A61K 35/78; A61K 9/14
(52) U.S. Cl. ........................ 424/757; 424/725; 424/489
(58) Field of Search ............................ 424/757, 195.1, 424/489, 725

(56) References Cited

U.S. PATENT DOCUMENTS

| | | | |
|---|---|---|---|
| 5,424,331 A | 6/1995 | Shylankevich | |
| 5,516,528 A | 5/1996 | Hughes | |
| 5,523,087 A | 6/1996 | Shylankevich | |
| 5,807,586 A | 9/1998 | Jackson et al. | |
| 5,904,924 A | * 5/1999 | Gaynor et al. | 424/195.1 |
| 5,906,982 A | * 5/1999 | Prieto et al. | 514/61 |

FOREIGN PATENT DOCUMENTS

| FR | 1519555 | * 7/1966 |
|---|---|---|

OTHER PUBLICATIONS

Setchell, et al., Nonsteroidal Estrogens of Dietary Origin: Possible Roles in Hormone–Dependent Disease, Am J Clin Nutr, 1984 Sep.; 40(3): 569–78.

Folman, et al., Effect of Norethisterone Acetate, Dimethylstilboestrol, Genistein and Coumestrol on Uptake of [$H^3$]oestradiol By Uterus, Vagina and Skeletal Muscle of Immature Mice, J. Endocrinol, 1969 Jun.; 44(2):213–8.

Kaziro, et al., The Oestrogenicity of Equol in Sheep, J. Endocrinol, 1984 Dec., 103(3):395–9.

Tang, et al., Effect of Equol on Oestrogen Receptors and on Synthesis of DNA and Protein in the Immature Rat Uterus, J. Endocrinol, 1980 May;85(2):291–7.

Adlercreutz, et al., Effect of Dietary Components Including Lignans and Phytoestrogens, on Enterohepatic Circulation and Liver Metabolism of Estrogens and On Sex Hormone Binding Globulin (SHBG), J Steroid Biochem, 1987;27(4–6):1135–44.

Mousavi, et al., Genistein is an Effective Stimulator of Sex Hormone–Binding Globulin Production in Hepatocarcinoma Human Liver Cancer Cells and Suppresses Proliferation of these Cells in Culture, Steroids, 1993 Jul.;58(7):301–4.

Arjmandi, et al., Dietary Soybean Protein Prevents Bone Loss in an Ovariectomized Rad Model of Osteoporosis [1,2], J Nutr, 1996 Jan.;126(1):161–7.

Messina, et al., Soy Intake and Cancer Risk: A Review of the In Vitro and In Vivo Data, Nutr Cancer, 1994;21(2):113–31.

Adlercreutz, et al., Soybean Phytoestrogen Intake and Cancer Risk, 1995 Mar.; 125(3 Suppl): 757S–770S.

Kennedy, et al., Essential Fatty Acids and USDA's Food Guide Pyramid, Am J Clin Nutr, 1995 Sep.;62(3):645–7.

Adlercreutz, et al., Dietary Phytoestrogens and Cancer: In Vitro and In Vivo Studies, J Steroid Biochem Mol Biol, 1992 Mar.; 41(3–8):331–7.

Anderson, et al., Meta–analysis of the Effects of Soy Protein Intake on Serum Lipids, N Engl J Med, 1995 Aug. 3;333(5):276–82.

Peterson, et al., Genistein Inhibition of the Growth of Human Breast Cancer Cells: Independence from Estrogen Receptors and The Multi–Drug Resistance Gene, Biochemical and Biophysical Research Communications, 1991, vol. 179, 661–667.

Peterson, et al., Genistein and Biochanin A Inhibit the Growth of Human Prostate Cancer Cells but not Epidermal Growth Factor Receptor Tyrosine Autophosphorylation, Prostate, 1993;22(4):335–45.

Barnes, et al., Soybeans Inhibit Mammary Tumors in Models of Breast Cancer, Mutagens and Carcinogens in the Diet, 1990; 239–253.

Vegetables, Fruits and Legumes: Effect on Urinary Isoflavonoid Phytoestrogen and Lignan Excretion, J Am Diet Assoc, 1995 Jul.; 95(7):769–74.

* cited by examiner

*Primary Examiner*—Christopher R. Tate
*Assistant Examiner*—Randall Winston
(74) *Attorney, Agent, or Firm*—Thorpe North & Western

(57) ABSTRACT

A composition for improving isoflavone metabolism and the bioavailability of phytoestrogens in warm blooded animals comprising a phytoestrogen, a dietary fiber, L-glutamine, and optionally N-acetyl-D-glucosamine, in admixture with a biologically acceptable inert carrier.

11 Claims, No Drawings

PREPARATION OF FIBER, L-GLUTAMINE AND A SOY DERIVATIVE FOR THE PURPOSE OF ENHANCEMENT OF ISOFLAVONE BIOAVAILABILITY

This application claims the benefit of U.S. Provisional Application No. 60/150,018 filed on Aug. 20, 1999.

BACKGROUND OF THE INVENTION

This invention relates to nutritional supplements. More particularly, the invention relates to a nutritional supplement composition, and methods of use thereof, to enhance the bioavailability of isoflavone.

Nearly 70 years ago, it was reported that certain plants could induce estrus in animals. Subsequently, over 300 plants have been found to possess estrogenic activity (see e.g., Bradbury and White, Vitamin Horm. 12:207 (1954), and Farnsworth et al., J. Pharm. Sci. 64:717(1954)). These compounds have been given the general name of "phytoestrogens" and represent several chemical classes of diphenolic plant compounds that are somewhat related structurally to the mammalian sex hormone 17-beta-estradiol. See Setchell, K. D. R., et al Am. J. Clin. Nutr., 40:569 to 578 (1984). Similarities in the molecular structure of phytoestrogens facilitate binding to the estrogen receptor. An important class of the phytoestrogens is the isoflavone class. Two chemical classes of phytoestrogens are abundant in soybeans, total soy products, and soy protein isolates. Those two classes are coumestrol and isoflavones. The latter class includes daidzein, genistein, glycitein, as well as their glycoside and acetylated forms.

Phytoestrogens and their metabolites interact with specific cell receptors and compete with endogenous hormone molecules [see Folman, Y. et al, J. Endocr., 44:213 to 218 (1969)], but the biological estrogen-like effect of these compounds is relatively weak. See Kaziro, R. et al, J. Endocr., 103:395 to 399 (1984) and Tang, B. Y. et al, J. Endocr. 85:291 to 297 (1980). Phytoestrogens can induce two different effects in an organism. When the level of endogenous sex hormones is relatively high, the antiestrogenic effect prevails. There are several mechanisms of antiestrogenic activity of the phytoestrogens, including feedback inhibition at the hypothalamus and pituitary gland, and competition and blockade of cell receptors. It has been observed that a phytoestrogen and lignan-rich diet is associated with a reduction in free plasma estradiol, and in reduction of the risk of breast cancer. See Adlercreutz, H. et al, J. Steroid. Biochem., 27:1135 to 1144 (1987) and Mousavi, Y. et al, Steroids, 58:301 to 304 (1993). On the other hand, in postmenopausal women, phytoestrogens can provoke an estrogenic response. See Adlercruetz, H. et al, Lancet, 339:1233 (1992). This dual effect of weak estrogens is demonstrated, and well known "partial" antigens such as Tamoxifen have these properties.

Phytoestrogens have been demonstrated in clinical trials to modulate the menstrual cycle, reduce menopausal symptoms, and lower LDL cholesterol levels. J. Nutr., 1996, 126(1): 161–7; N. Engl. J. Med., 1995, 333: 276–82. Epidemiologic observations indicate women in countries where diets are rich in phytoestrogens (averaging about 40–50 mg/day) have a decreased incidence of breast cancer, menopausal symptoms and osteoporosis. Nutr. Cancer, 1994, 21:113–131; J. Nutr., 1995,125; 757S--770S; Am. J. Clin. Nutr. 1995,62:645. Animal studies have provided a biological basis for these observations. J. Ster. Biochem & Mol. Bio., 1992, 41(3–8): 331–7; First International Symposium on the role of Soy and Preventing and Treating Chronic Disease (1994), Speaker Abstracts.

Soybeans are a particularly important source of phytoestrogens. Several hundred varieties or cultivars of soybeans exist, and their phytoestrogen content can vary from 50 mg/100 g to 300 mg/100 g. In addition, given the high levels of consumption of soy protein by certain Oriental cultures, there is a substantial body of relevant epidemiologic evidence. For example, there is epidemiologic evidence that phytoestrogens are associated with a lower risk of development of breast and uterine cancer. Experimental evidence for lower breast cancer incidence associated with dietary intake of phytoestrogens in soybeans has also been reported (Barnes et al., In Jacobs M M, ed., Diet and Cancer: Markers, prevention and treatment, New York: Plenum Press, 135 (1994)). Specifically, dietary soy protein preparations enriched with phytoestrogens inhibited mammary tumors in rats treated with 7,12-dimethyl-benz[a]anthracene compared to rats fed low-phytoestrogen soy protein preparations.

The increasingly frequent suggestion that phytoestrogens may protect against development of coronary artery atherosclerosis (CAA) and coronary heart disease(CHD) is based on the evidence that endogenous estrogen protects premenopausal women from CHD relative to men of the same age, that loss of ovarian hormones accounts for the increase in CHD in postmenopausal women, and that estrogen replacement decreases CHD risk among postmenopausal women.

In addition to the epidemiological evidence, recent experimental observations have suggested that phytoestrogens may protect against the development of CAA. For example, studies have shown that male casein-fed rats had significantly higher total plasma cholesterol (TPC) and low density lipoprotein cholesterol (LDL-C) concentrations than soy protein-fed rats. When soybean phytoestrogens were added to casein, the animals had LDL-C concentrations similar to the soy protein-fed group.

It has been recently recognized that the isoflavones contained in vegetable proteins, such as soybeans, may inhibit the growth of human cancer cells, such as breast cancer cells and prostrate cancer cells, and is described in the following articles: "Genistein Inhibition of the Growth of Human Breast Cancer Cells; "Independence from Estrogen Receptors and the Multi-Drug Resistance Gene" by Peterson and Barnes Biochemical and Biophysical Research, Communications; Vol. 179, No. 1, pp. 661–667, Aug. 30, 1992; "Genistein and Biochanin A Inhibit the Growth of Human Prostate Cancer Cells but not Epidermal Growth Factor Receptor Tyrosine Auto-phosphorylation" by Peterson and Barnes: The Prostate 22: pp. 335–345 (1993) and "Soybeans Inhibit Mammary Tumors in Models of Breast Cancer" by Barnes, et al. Mutagens and Carcinogens in the Diet; p. 239–253 (1990).

Isoflavones have been added to nutritional supplements for a variety of therapeutic purposes as shown in U.S. Pat. Nos. 5,523,087; 5,424,331; 5,516,528 and 5,807,586. The bioavailability in human subjects of dietary isoflavones is of great importance relative to their biofunctional effects. Once ingested, several factors influence the bioavailability of isoflavones. Simply adding phytoestrogen-rich foods to the diet may not ensure effective bioavailability because isoflavones cannot work unless they are first converted to biologically active estrogen-like compounds by friendly intestinal bacteria. Since the presence of friendly bacteria is, in turn, dependent upon a healthy gastrointestinal climate, all the dietary and lifestyle factors that affect the digestive tract can have significant impact on the bioavailability of dietary isoflavones.

In view of the foregoing, there is a need for a composition for the enhancement of isoflavone bioavailability in human beings and other warm blooded animals that improves digestive tract environment.

BRIEF SUMMARY OF THE INVENTION

The present invention provides a composition and a method for improving the gastrointestinal climate for beneficial microorganism growth in warm blooded animals.

The present invention also provides a composition and a method for improving isoflavone metabolism and the bioavailability of phytoestrogens in warm blooded animals.

One embodiment of the present invention is a dietary supplement composition for administration to warm blooded animals comprising a fiber, L-glutamine and a phytoestrogen.

Another embodiment of the present invention is a method for improving the gastrointestinal climate for friendly bacterial growth and the bioavailability of phytoestrogen comprising the steps of administering effective amounts of a composition comprising fiber, L-glutamine and a phytoestrogen.

DETAILED DESCRIPTION

Before the present composition and methods of making and using thereof are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise.

Herein there is described a composition and a method of use thereof to improve the gastrointestinal climate for friendly bacterial growth in warm blooded animals and to enhance the bioavailability of phytoestrogens, which comprises the step of administering effective amounts of a composition comprising a fiber, L-glutamine, and a phytoestrogen. Improvement of the gastrointestinal climate for friendly bacterial enhances beneficial bacteria growth, which in turn enhances the metabolism and bioavailability of phytoestrogens, such as isoflavones.

As used herein, "subject" refers to any mammal, including humans. The methods herein for use on subjects contemplate prophylactic use as well as curative use as part of therapy for an existing condition.

The term "phytoestrogen" as used herein represents several chemical classes of diphenolic plant compounds that are somewhat related structurally to the mammalian sex hormone, 17-β-estradiol. Two chemical classes of phytoestrogens are abundant in soybeans, total soy products, and soy protein isolates. Those two classes are coumestrol and isoflavones. The isoflavone class includes daidzein, genistein, glycitein, as well as their glycoside and acetylated forms. Therefore, when the present invention refers to enhancement of the bioavailability of isoflavones, it means phytoestrogen isoflavones including daidzein, genistein, glycitein, as well as their glycoside and acetylated forms and other functional derivatives, which are all within the scope of the present invention.

The term "probiotic microorganism" or "friendly bacteria" as used herein represents microorganisms and bacteria in the gastrointestinal tract which help absorption and metabolism of phytoestrogens and so are beneficial to the host. There are three main kinds of beneficial bacteria, i.e. Bifidobacterium, *Lactobacillus acidophilus* and *Lactobacillus bulgaricus*.

The definition of the term "fiber" and "dietary fiber" as used herein includes unavailable carbohydrates, indigestible residue, and plant cell polysaccharides and lignin, all of which are resistant to hydrolysis by human digestive enzymes. Preferred fibers are members selected from the group consisting of guar gum, pectin, fructo-oligosaccharides and derivatives thereof. Small amounts of other indigestible compounds, such as phytates, tannins, saponins and cutin, may be included in dietary fiber since these compounds are indigestible and associated with dietary fiber polysaccharides.

As used herein, "effective amount" means an amount of the component of the composition of the present invention sufficient to provide the selected local or systemic effect and performance at a reasonable benefit/risk ratio that would attend any acceptable medical treatment.

As used herein, "administering", and similar terms mean delivering the multi-nutritional supplemental composition, according to the present invention, to the subject being treated such that the composition is capable of being circulated systemically to the parts of the body where the composition can contact the target cells. Thus, the composition is preferably orally administered to the individual.

The invention, in one of its most general embodiments, concerns a composition and a method of use thereof to enhance the bioavailability of phytoestrogens by improving the gastrointestinal climate for friendly bacterial growth. The composition comprises a fiber, L-glutamine and a phytoestrogen. Preferably, a daily dosage form of the composition will comprise 100 mg to 20 gms of fiber, 25 mg to 10 gms of L-glutamine, 25 to 1000 mg of phytoestrogen, and optionally, 25 mg to 1000 mg of N-acetyl-D-glucosamine. More preferably, a daily dosage form of the composition will comprise 80 mg to 15 gms of fiber, 20 mg to 5 gms of L-glutamine,20 to 1000 mg of phytoestrogen, and optionally, 25 mg to 100 mg of N-acetyl-D-glucosamine. The weight ratio of the phtoestrogen, the dietary fiber and the L-glutamine is within a range of about 1:4:1 to 1:20:10, and preferably within a range of 1:4:1 to 1:15:5. The daily dosage form may be formulated as a single dosage or as multiple dosages which be administered at time intervals throughout the day.

There are two classes of phytoestrogens, isoflavones and coumestans, that are especially contemplated to be within the scope of the present invention. Examples of the isoflavones include daidzein, genistein, glycitein, and their glycosides: daidzin, genistin, and glycitin, as well as acetylated forms of the above mentioned compounds. An example of a coumestan is coumestrol.

In plants, isoflavones are inactive when present in the bound form as glycosides, but when the sugar residue is removed, these compounds become activated. These plant compounds undergo fermentation by intestinal microflora, with both metabolites and unfermented parent (aglycone) compounds being liable to absorption. In the body the parent compounds are reconjugated to glucuronides, but otherwise do not undergo any further metabolism in the body and are excreted in the urine. Daidzein may be metabolized the colonic microflora to equol or to O-demethyl-angolensin (O-Dma) and genistein may be metabolized to p-ethyl phenol. Daidzein, genistein, equol, and O-Dma are the major phytoestrogens detected in the blood and urine of humans and animals.

Once ingested several factors influence the bioavailability of isoflavones. For example, when assessed for urinary isoflavone recovery in postmenopausal women consuming either tempeh, a fermented soybean product, or a comparable quantity of soybean pieces from an unfermented soybean product, urinary isoflavone recovery was greater for the tempeh. The presence of fiber in the diet has been shown to correlate positively with urinary excretion of phytoestrogens. Several investigators have reported that individual variability in colonic microflora plays an important role in determining the preferred pathways of isoflavone metabolism and the bioavailability of isoflavones.

Bifidogenic factors are those elements that help the body increase its levels of beneficial bacteria. These include substances such as N-acetylglucosamine, lactulose found in milk and milk products, and fructooligosaccharides(FOS). One critical factor influencing the bioavailability of isoflavones is soluble fiber, a primary food source for the friendly intestinal bacteria *Lactobacillus acidophilus* and *Bifidobacterium bifidus*. Without an adequate supply of food that they specifically live on, these friendly bacteria cannot thrive. This also explains why antibiotics frequently contribute to female health problems, since antibiotics destroy both the bacterial infection for which they are prescribed and a woman's friendly intestinal flora, which allows other unfriendly flora to proliferate. As a result, a woman taking tetracycline for acne may find herself dealing with vaginal yeast infections and post-menopausal-syndrome (PMS). An imbalance in bowel flora can lead to an imbalance in circulating estrogen.

Diets high in soluble and insoluble fiber and low in fat (less than 25 percent of daily calories) result in a significant increase in levels of hormonally activated phytoestrogens as reported in the American Journal of Clinical Nutrition, 1989, vol. 49, and the American Journal of Nutrition, 1991, vol. 54. The examples of such beneficial fiber include apple pectin, guar gum, fructooligosaccharides (FOS). FOS are a class of sucrose molecules (glucose-fructose disaccharides) to which one, two or three additional fructose molecules have been added. FOS are nutrients that sustain and stimulate helpful microorganisms. It is of interest that the digestive system does not break down FOS. Rather, they reach the lower intestines intact where they are devoured by the "friendly bacteria" without significantly assisting any of the "unfriendly bacteria."

Dietary fiber has a considerable effect on function and morphology throughout the gastrointestinal tract. The effect of fiber on the intestinal tract is in part a function of residence or transit time. Fibers also affect the mucosal, absorptive ability and luminal contents throughout the gastrointestinal tract. Many of the effects of ingested fiber on the colon relate in part to its being broken down in this portion of the gut. Such fiber breakdown is an anaerobic process and is called fermentation. For every 20 gm of fiber broken down in the human colon each day, approximately 200 mM of short chain fatty acid (SCFA) will be produced, of which about 62 percent will be acetate, 25 percent propionate, and 16 percent butyrate. The SCFA produced by colonic fermentation of dietary residues, such as soluble fiber and undigested starch, are the fuels preferred by the colonic mucosa.

The gastrointestinal tract, like all tissues, requires nutrients to support cell turnover and metabolism. Failure to maintain normal mucosal structure can lead to impaired barrier function in the gut and increased intestinal permeability. If marked mucosal atrophy has occurred, the reintroduction of enternal nutrients may be difficult. Preservation of the gut mucosa may prevent infection, limit morbidity, and enhance absorption and metabolism of nutrients.

It has been proposed that glutamine-containing nutrition solutions could provide specific nutritional support for gastrointestinal tissues. Additional studies have revealed the importance of short chain fatty acids as being preferentially utilized by the colonocyte. It has been reported that specific fuels, such as glutamine and short chain fatty acids have stimulatory effects on intestinal structure and function.

The massive turnover of cells within the gastrointestinal tract requires a constant supply of readily available energy. Trophic effects of diamines, free fatty acids, and pectin have been clearly demonstrated. Increasing evidence suggests that dietary amines promote direct, nonhormonal stimulation of specific mucosal enzymes, such as ornithine decarboxylase. These enzymes are required for polyamine biosynthesis, and their suppression leads to inhibition of mucosa DNA synthesis.

The intestine is a major site of glutamine consumption and, in turn, has high glutaminase activity. Glutamine provides nitrogen for a number of biosynthetic pathways, serving as a precursor to the purine and pyrimide rings of nucleic acids and nucleotides, and is an important constituent of proteins and a precursor of amino sugars. Although it has been known for many years that glutamine is essential for growth of many types of rapidly dividing cells in culture, it later became apparent that enterocytes and colonocytes actively and preferentially metabolize this amino acid.

The increase in intestinal cellularity that occurs when glutamine is added to nutrition solutions suggests that inadequate nutrient delivery plays a part in the intestinal atrophy associated with parenteral feeding. It is not yet clear whether glutamine has its impact on the intestine as a metabolic fuel, as a precursor of metabolites that are essential for cellular replication, or as a regulator of enterotrophic hormones. The relationship between glutamine and growth factors in the gut is speculative at the present time, but studies have indicated that glutamine may interact with specific growth factors.

While maximal glutamine uptake is by the enterocytes of the small intestine, colonocytes also have the capacity to utilize short chain fatty acids(SCFA) which are produced in the mammalian intestinal tract as by-products of anaerobic bacterial fermentation of polysaccharides found in dietary fiber. In nonruminants most of this fermentation occurs in the cecum and colon. The straight chain fatty acids of acetate, propionate, and butyrate are the major end-products of bacterial carbohydrate metabolism in the colon.

As mentioned previously, dietary fiber and resistant starch are the principal substrates for hindgut SCFA production in nonruminants, and therefore colonic SCFA production can be altered by changing the dietary content of these substances. The three major SCFAs, once absorbed, are metabolized by the cecal and colonic mucosa. One result of production, absorption, and metabolism of the SCFA is the provision of energy to the host. It has been estimated that the absorption of SCFA from fiber fermentation may provide from 5 to 30 percent of the daily energy requirements.

In summary, glutamine is not only essential for the growth of many types of rapidly dividing cells in culture, it has been also well documented that enterocytes and colonocytes actively and preferentially metabolize this amino acid.

Unlike other tissues, the gut has adapted to preferentially metabolize glutamine since the free ammonia produced readily diffuses into the portal blood and is extracted by the liver before reaching the systemic circulation. Glutamine is metabolized similarly whether it enters the mucosal cells from the lumen or from the blood. When fiber polysaccharide residue reaches the cecum(residue that cannot be digested by the enzymes of the upper gastrointestinal tract), it produces short chain fatty acids(SCFA) as by-products of bacterial fermentation. SCFA are the preferred respiratory fuels for the colonic mucosa. Therefore, according to the present invention the combination of glutamine, fiber and a phytoestrogen provides an improved metabolic environment for enterocytes and colonocytes, which in turn enhances the metabolism and bioavailability of phytoestrogens.

The compositions of this invention may contain single or combinations of phytoestrogens. A preferred combination of the phytoestrogens includes daidzin and genistin having a molar ratio of between about 15:1 to about 1:1. As a possible variant, the combination can include daidzin and genistin in equimolar concentrations. At least 2%(by weight) of the phytoestrogens can be in forms of aglycones. The dosage amount of total isoflavones(genistein, daidzein and glycitein) can vary from about 25 mgs to about 1,000 mgs daily.

These compositions may also include a non-toxic inert carrier or diluent in admixture with the above mentioned active ingredients. Examples of such non-toxic, inert carriers include wheat starch, sodium carboxymethyl cellulose, cellulose, maltodextrin, fructose, sucrose, soy flour, sorbitol, mannitol, and corn syrup.

The administration of the composition of the present invention, which enhances isoflavone availability, would be in accordance with a predetermined regimen. This would be at least once weekly, preferably on a daily basis and over an extended period of time, generally for at least one month, more usually for at least three months, and as a chronic treatment that could last for one year or more, possibly including the life of the subject. There are no restrictions on age and duration for using the new compositions as dietary supplements.

The dose administered will depend upon the frequency of administration, the blood level desired, other concurrent therapeutic treatments, the severity of the condition, whether the treatment is for prophylaxis or therapy, and the like. The amount of phytoestrogen(e.g. isoflavones) administered per day may be within a range of 25 mg to 1000 mg, preferably 200 mg, which corresponds to the amount of isoflavones naturally occurring in 50–75 g of raw soybeans. This is the average amount of soybeans consumed daily in an Oriental diet. A 200 mg dose of isoflavones is functionally equivalent to the average daily dose of conjugated steroidal estrogen used in hormone replacement therapy. When the above mentioned compositions are administered to a mammalian subject for therapeutical purposes, they are preferably administered orally in a dose of 0.15 to 35 g of active ingredients per day. By active ingredients, it does not mean only the phytoestrogens, but also the fiber and glutamine mentioned in the compositions as well. The optimum dosage of course depends on the body weight of the subject as well as the therapeutic purpose of the administration.

When the mammalian subject is a human, the daily dosage of the composition should be within the following ranges: 0.15 to 35 grams per day. More preferably, the daily dosage of the composition administered is within a range of 1 to 35 grams. The most preferred administration regimen of the composition of the present invention is daily dosage of 2–30 grams.

The compositions may also be employed as dietary supplements for mammalian subjects. When the new compositions are employed as dietary supplements, they are preferably administered orally as tablets or capsules, or they may be mixed with food.

The composition of this invention may be made in a variety dosage forms, such as tablets, pills, capsules, powders, solutions, dispersions, food products, and the like. The composition is formulated with physiologically acceptable carriers and optionally stabilizers, colorants, and flavoring agents.

When the new compositions are employed as dietary supplements, they may be admixed with the mammalian subject's food rather than given as individual compositions in tablet or capsule form. Dietary wafers and liquid supplements which contain all of the active ingredients of the dietary supplement in unit dosage form are especially contemplated.

The following examples will enable those skilled in the art to more clearly understand how to practice the present invention. It is to be understood that while the invention has been described in conjunction with the preferred specific embodiments thereof, that which follows is intended to illustrate and not limit the scope of the invention. Other aspects of the invention will be apparent to those skilled in the art to which the invention pertains.

EXAMPLE I

Over a two-month study period, ten subjects were supplemented with 50 mgs of isoflavones daily for one month. Then, for the second month, the same subjects were supplemented daily with the composition of the present invention which contained 50 mgs of isoflavones enriched with an admixture containing a 350 mg blend of glutamine, FOS, guar gum, apple pectin and N-acetyl-D-glucosamine. Urinary recovery assays of isoflavones were performed by routine laboratory procedures known in the art. A method of isoflavone assay is described in Hutchings A M, et al. Vegetables, fruits, and legumes: effect on urinary isoflavonoid phytoestrogen and lignan excretion. J Am Diet Assoc. 95:769–774, and is incorporated herein by reference. The urinary recovery of ingested isoflavones during the first month(isoflavone alone) were, on the average, 66% of that recovered when administering the enriched isoflavones of the present invention. This indicates that the enriched isoflavone composition of the present invention enhances the bioavailability of isoflavones by about 34%.

EXAMPLE II

Over a two-month study period, ten subjects were supplemented with 50 mgs of isoflavones daily for one month. Then, for the second month, the same subjects were supplemented daily with the composition of the present invention containing 50 mgs of isoflavones enriched with an admixture containing a 2000 mg blend of glutamine, FOS, guar gum, apple pectin and N-acetyl-D-glucosamine. Urinary recovery assays of isoflavones were performed by routine laboratory procedures known in the art. The urinary recovery of ingested isoflavones during the first month(isoflavone alone) were, on the average, 17% of that recovered when the enriched isoflavones of the present invention were administered. This indicates that the enriched isoflavone composition of the present invention enhances the bioavailability of isoflavones by about 83%.

EXAMPLE III

In this Example, seven healthy women were supplemented daily with the composition of the present invention containing 75 mgs of isoflavones enriched with an admixture containing a 350 mg blend of glutamine, FOS, guar gum, apple pectin and Nacetyl-D-glucosamine. For five of the seven women with less then 1% fecal recovery of isoflavones, the amount of urinary recovery was 12–15%. For the other two women with a greater fecal recovery of at least 5%, the amount of urinary recovery was 26–31%. These data suggest that both absorption and intestinal degradation are important factors in determining bioavailability. These data also support the observation that there is substantial individual variability in isoflavone metabolism.

Thus, among the various formulations taught there has been disclosed composition and a method of use thereof to enhance the bioavailability of phytoestrogens by improving the gastrointestinal climate for friendly bacterial growth. The composition comprises a fiber, L-glutamine and a phytoestrogen. It will be readily apparent to those skilled in the art that various changes and modifications of an obvious nature may be made without departing from the spirit of the invention, and all such changes and modifications are considered to fall within the scope of the invention as defined by the appended claims. Such changes and modifications would include, but not be limited to, the incipient ingredients added to affect the capsule, tablet, lotion, food or bar manufacturing process as well as vitamins, herbs, flavorings and carriers. Other such changes or modifications would include the use of other herbs or botanical products containing the combinations of the present invention disclosed above.

We claim:

1. A composition to increase the bioavailability of phytoestrogens comprising effective amounts of: a phytoestrogen, a dietary fiber and L-glutamine, wherein ratio of the phytoestrogen, the dietary fiber and the L-glutamine is within a range of 1:4:1 to 1:20:10.

2. The composition to increase the bioavailability of phytoestrogens according to claim 1 wherein ratio of the phytoestrogen, the dietary fiber and the L-glutamine is with in a range of 1:4:1 to 1:15:5.

3. The composition of claim 1 wherein the composition is in a dosage form selected from the group consisting of tablets, pills, capsules, powders, solutions, dispersions, food products and equivalents thereof.

4. The composition of claim 1 wherein the phytoestrogen is soy-derived.

5. The composition of claim 4 wherein the phytoestrogen is an isoflavone.

6. The composition of claim 5 wherein the phytoestrogen is a mixture of genistein and daidzein with a ratio from 15:1 to 1:1, and at least 2% (w/w)of aglycones.

7. The composition of claim 1 wherein the fiber is a dietary fiber selected from the group consisting of pectin, guar gum, fructo-oligosaccharides and the mixture thereof.

8. The composition of claim 7 wherein the dietary fiber is pectin.

9. The composition of claim 7 wherein the dietary fiber is guar gum.

10. The composition of claim 7 wherein the dietary fiber is fructo-oligosaccharide.

11. The composition of claim 1 further comprising N-acetyl D-glucosamine.

* * * * *